(12) United States Patent
Ueno et al.

(10) Patent No.: US 6,461,749 B2
(45) Date of Patent: Oct. 8, 2002

(54) ORGANIC BORON COMPOUND, PROCESS FOR PRODUCING THE COMPOUND AND ORGANIC LUMINESCENCE DEVICE USING THE COMPOUND

(75) Inventors: Kazunori Ueno, Ebina; Koichi Suzuki, Yokohama; Akihiro Senoo, Kawasaki; Hiroshi Tanabe, Yokohama; Seiichi Yogi, Naha, all of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/818,661

(22) Filed: Mar. 28, 2001

(65) Prior Publication Data

US 2002/0008465 A1 Jan. 24, 2002

(30) Foreign Application Priority Data

Mar. 31, 2000 (JP) ........................................ 2000-096322

(51) Int. Cl.[7] ........................ H05B 33/12; C07D 213/02
(52) U.S. Cl. ........................ 428/690; 428/917; 313/504; 313/506; 546/13
(58) Field of Search ................................. 428/690, 917, 428/704; 313/504; 546/13; 568/1

(56) References Cited

U.S. PATENT DOCUMENTS

| 4,539,507 A | 9/1985 | VanSlyke et al. ............ 313/504 |
| 4,720,432 A | 1/1988 | VanSlyke et al. ............ 428/457 |

(List continued on next page.)

FOREIGN PATENT DOCUMENTS

| JP | 09289081 A | * 11/1987 | ............ H05B/33/14 |
| JP | 2-216791 | 8/1990 | |

(List continued on next page.)

OTHER PUBLICATIONS

*Appl. Phys. Lett.*, vol. 51, pp. 913–915 (1987).
J. H. Burroughes et al., "Light–Emitting Diodes Based on Conjugated Polymers," 347 *Nature* 539–541 (1990).

*Primary Examiner*—Cynthia H. Kelly
*Assistant Examiner*—Dawn Garrett
(74) *Attorney, Agent, or Firm*—Fitzpatrick, Cella, Harper & Scinto

(57) ABSTRACT

An organic boron compound effective for constituting a functional layer in an organic luminescence device is represented by formula (1) below:

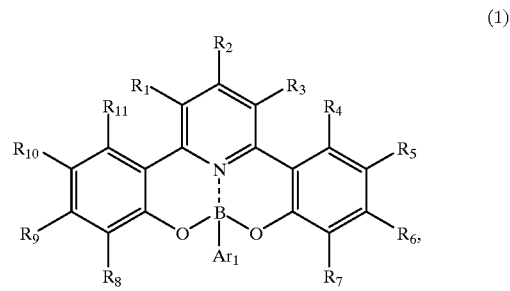

(1)

wherein $Ar_1$ denotes an optionally substituted aryl group or heterocyclic group; $R_1$–$R_{11}$ independently denote hydrogen, halogen, alkyl, alkenyl, amino, alkoxy, formyl, nitrile, aroyl, alkyloyl, aryl, aralkyl or heterocyclic group, each optionally substituted with the proviso that an adjacent one or more pairs of $R_1$–$R_{11}$ can form a condensed ring. The organic boron compound can be produced through a process including (A) a step of reacting an aromatic ketone compound X with an aromatic ketone compound or an aromatic aldehyde compound in the presence of ammonium chloride, and (B) a step of reacting a product of the step (A) with an aromatic boric acid compound.

13 Claims, 2 Drawing Sheets

U.S. PATENT DOCUMENTS

| | | | | |
|---|---|---|---|---|
| 4,885,211 A | 12/1989 | Tang et al. | ................. | 428/457 |
| 5,130,603 A | 7/1992 | Tokailin et al. | ............. | 313/504 |
| 5,151,629 A | 9/1992 | VanSlyke | .................... | 313/504 |
| 5,227,252 A | 7/1993 | Murayama et al. | ......... | 428/690 |
| 5,247,190 A | 9/1993 | Friend et al. | ................. | 257/40 |
| 5,317,169 A | 5/1994 | Nakano et al. | ............... | 257/40 |
| 5,382,477 A | 1/1995 | Saito et al. | ................. | 428/690 |
| 5,409,783 A | 4/1995 | Tang et al. | ................. | 428/690 |
| 5,514,878 A | 5/1996 | Holmes et al. | ............... | 254/40 |
| 5,672,678 A | 9/1997 | Holmes et al. | ............. | 528/373 |
| 5,869,199 A | 2/1999 | Kido | ......................... | 428/690 |

FOREIGN PATENT DOCUMENTS

| | | |
|---|---|---|
| JP | 2-247278 | 10/1990 |
| JP | 3-255190 | 11/1991 |
| JP | 4-145192 | 5/1992 |
| JP | 4-363891 | 12/1992 |
| JP | 5-202356 | 8/1993 |
| JP | 5-247460 | 9/1993 |
| JP | 7-41759 | 2/1995 |
| JP | 7-90260 | 4/1995 |
| JP | 9-202878 | 8/1997 |
| JP | 9-227576 | 9/1997 |

* cited by examiner

ORGANIC BORON COMPOUND, PROCESS FOR PRODUCING THE COMPOUND AND ORGANIC LUMINESCENCE DEVICE USING THE COMPOUND

FIELD OF THE INVENTION AND RELATED ART

The present invention relates to a novel organic boron compound, a process for production thereof and an organic (electro-)luminescence device using the organic boron compound.

An organic luminescence device generally comprises a pair of electrodes (comprising an anode and a cathode) and a film comprising a fluorescent organic compound disposed between the electrodes. Into the organic compound layer (film), holes and electrons are injected from the anode and the cathode, respectively, thus forming excitons of the fluorescent organic compound. When the excitons are returned to ground state, the organic luminescence device emits light or causes luminescence.

According to a study by Eastman Kodak Co. ("Appl. Phys. Lett.", vol. 51, pp. 913-(1987)), it has been reported that a function-separation type organic luminescence layer comprising mutually laminated two layers including a layer of an aluminum quinolinol complex (as an electron transporting and luminescent material) and a layer of a triphenylamine derivative (as a hole transporting material) causes luminescence at a luminance (brightness) of ca. 1,000 cd/m$^2$ under application of a voltage of ca. 10 volts. This is also reported in, e.g., U.S. Pat. Nos. 4,539,507; 4,720,432 and 4,885,211.

Further, by changing species of the fluorescent organic compound, it is possible to effect luminescence over broad wavelength regions ranging from an ultraviolet region to an infrared region. In this regard, various compounds have been extensively studied in recent years. Such compounds have been proposed in, e.g., U.S. Pat. Nos. 5,151,629, 5,409,783 and 5,382,477, and Japanese Laid-Open Patent Applications (JP-A) 2-247278, JP-A 3-255190, JP-A 5-202356, JP-A 9-202878 and JP-A 9-227576.

In addition to the above-mentioned organic luminescence devices using low-molecular weight materials, an organic luminescence device using a conjugated polymer has been reported by a research group of Cambridge University ("Nature", vol. 347, pp. 539-(1990)). According to this report, a single layer of polyphenylenevinylene (PPV) is formed through a wet-coating process and luminescence from the single layer is confirmed. Such an organic luminescence device using a conjugated polymer has also been proposed by, e.g., U.S. Pat. Nos. 5,247,190, 5,514,878 and 5,672,678, JP-A 4-145192, and JP-A 5-247460.

As described above, recent progress in organic luminescence devices is noticeable, and the resultant organic luminescence devices are characterized by high luminance (brightness) under application of a low voltage, various (light-) emission wavelengths, high-speed responsiveness, small thickness and light weight, thus suggesting a possibility of wide applications.

However, the above-described organic luminescence devices are still required to effect light output (emission) at a higher luminance and/or a higher conversion efficiency in the present state. These organic luminescence devices are also still insufficient in terms of durability such that the devices are liable to be changed in their properties with time when used for a long period or liable to be deteriorated by the influence of ambient air containing oxygen or of humidity.

Further, as electron-injecting materials, there have been known: oxadiazole derivatives (JP-A 2-216791, JP-A 4-363891, etc.) and triazine derivatives (JP-A 7-41759, JP-A 7-90260, etc.). When used in an organic luminescence device, however, such an electron-injecting material is not fully satisfactory regarding provision of a stable layer or a sufficient electron injection efficiency. The luminescence intensity or the life is not sufficient either.

SUMMARY OF THE INVENTION

A generic object of the present invention is to provide an improvement to the above-mentioned state of the art.

A more specific object of the present invention is to provide a novel organic boron compound and a process for production thereof.

Another object of the present invention is to provide an organic luminescence device capable of high luminance light emission at a high efficiency while exhibiting a long life.

Another object of the present invention is to provide an organic luminescence device capable of emitting a diversity of luminescence wavelengths and exhibiting various luminescence hues with a very excellent durability.

A further object of the present invention is to provide an organic luminescence device, which can be produced easily and be relatively inexpensive.

According to the present invention, there is provided an organic boron compound represented by formula (1) below:

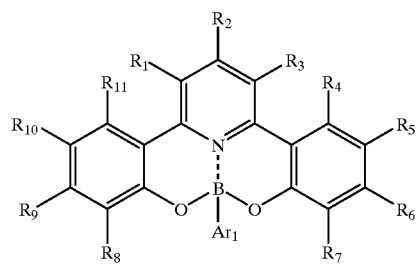

(1)

wherein $Ar_1$ denotes an optionally substituted aryl group or heterocyclic group; $R_1$–$R_{11}$ independently denote hydrogen, halogen, alkyl, alkenyl, amino, alkoxy, formyl, nitrile, aroyl, alkyloyl, aryl, aralkyl or heterocyclic group, each optionally substituted with the proviso that an adjacent one or more pairs of $R_1$–$R_{11}$ can form a condensed ring.

According to the present invention, there is also provided a process for producing an organic boron compound of the above formula (1), comprising:

(A) a step of reacting a ketone compound X with a ketone compound Y or an aldehyde compound in the presence of ammonium chloride, and (B) a step of reacting a product of the step (A) with an organic boric acid compound.

The present invention further provides an organic luminescence device, comprising: a pair of electrodes comprising an anode and a cathode, and a layer of organic compound disposed between the electrodes; wherein the organic compound layer comprises an organic boron compound of the above formula (1).

The organic boron compound of the present invention exhibits a strong fluorescence characteristic and is useful as a luminescent material for a luminescence device.

The process of the present invention allows easy production of the organic boron compound.

The organic boron compound of the present invention is useful for constituting an electron-transporting layer or/and a luminescence layer, and is also useful for constituting an electron-injecting layer.

The organic luminescence device of the present invention is characterized by its capability of having an extremely high-luminance luminescence at a low application voltage, excellent durability, and also the capability to emit luminescence of various hues. For example, the organic luminescence device can cause luminance of primary colors, red, blue and green, and is therefore promising as a display device. Further, the device can be produced generally through vacuum deposition or casting, so that a large-area device can be easily produced at a relatively low cost.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
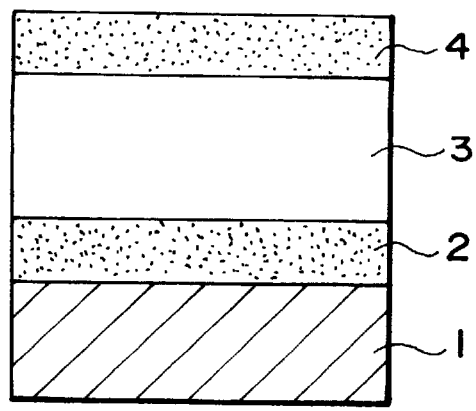
FIGS. 1 to 3 are schematic sectional views each illustrating a basic structure of an organic luminescence device according to an embodiment of the present invention.

The organic boron compound of the present invention is represented by formula (1) below:

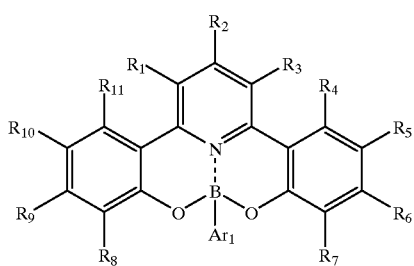

(1)

In the formula (1), $Ar_1$ denotes an optionally substituted aryl group or heterocyclic group.

Examples of the aryl group may include: monocyclic groups, such as phenyl, tolyl, aminophenyl, nitrophenyl, and halogenated phenyl; and polycyclic aromatic group, such as biphenyl, terphenyl, naphthyl, and anthranyl.

Examples of the heterocyclic group may include: monocyclic heterocyclic groups, inclusive of pyridyl, and 5-membered ring groups, such as pyrrolyl, thienyl, imidazolyl and pyrazolyl; and condensed heterocyclic group inclusive of 6,6-condensed heterocyclic groups, such as quinolyl and acridinyl, and 6,5-condensed heterocyclic groups, such as indolinyl.

Further, examples the substituents optionally possessed by the aryl or heterocyclic group may include: halogen, alkyl, alkoxy, amino, imino, acetyl, formyl, nitro, silyl, aryl, heterocyclic group, and nitrile. More specifically, the halogen substituents may include chloro, bromo, fluoro and iodo; the alkyl substituents may include linear alkyls such as methyl, ethyl and propyl; branched alkyls such as isobutyl and isopropyl, and substituted alkyls inclusive of aralkyl, such as benzyl; the aminoalkoxy substituents may include methoxy and ethoxy; the amino substituents may include secondary amino groups and ternary amino groups; the silyl substituents may includes dimethylsilyl, diphenylsilyl and t-butyldiphenylsilyl; the aryl substituents may include optionally substituted monocyclic groups such as phenyl, and optionally substituted polycyclic aromatic group such as biphenyl, terphenyl, naphthyl and anthranyl. The heterocyclic group substituents may include monocyclic heterocyclic groups such as quinolyl, pyrrolyl and thienyl, and condensed heterocyclic groups inclusive of 6,6-condensed heterocyclic groups such as acridinyl, and 6,5-condensed heterocyclic groups such as indolinyl.

On the other hand, the substituents $R_1$–$R_{11}$ independently denote hydrogen, halogen alkyl, alkenyl, amino, alkoxy, formyl, nitrile, aroyl, alkyloyl, aryl, aralkyl or heterocyclic group, each optionally substituted with the proviso that an adjacent one or more pairs of $R_1$–$R_{11}$, i.e., a pair of $R_1$ and $R_2$, $R_2$ and $R_3$, $R_3$ and $R_4$, $R_4$ and $R_5$, $R_5$ and $R_6$, $R_6$ and $R_7$, $R_8$ and $R_9$, $R_9$ and $R_{10}$, $R_{10}$ and $R_{11}$, or $R_{11}$ and $R_1$, can form a condensed ring.

Specific examples of the substituents $R_1$–$R_{11}$ are enumerated below.

Examples of the halogen may include: chloro, bromo, fluoro and iodo.

Examples of the alkyl may include linear or branched alkyl groups having 1 to 20 carbon atoms, inclusive of linear alkyl groups, such as methyl, ethyl, n-propyl, n-octyl and n-decyl; and branched alkyl groups, such as isopropyl and t-butyl.

Examples of the alkenyl may include: vinyl.

Examples of the amino may include: non-substituted amino; mono-substituted amino groups substituted with one alkyl, aralkyl or aryl; and di-substituted amino groups substituted with two of alkyl, aralkyl and aryl groups. Examples of the substituent alkyl groups may include: linear alkyls, such as methyl, ethyl, n-propyl, n-octyl and n-decyl; and branched alkyls, such as isopropyl and t-butyl.

Examples of the alkoxy may include: alkyloxy groups and aromatic oxy groups, such as methoxy, ethoxy and phenyloxy.

Examples of the aroyl may include: benzoyl, naphthoyl and anthroyl.

Examples of the alkyloyl may include: linear or branched aliphatic carbonyl groups, such as acetyl, n-propionyl, and isobutyroyl; and cyclic aliphatic carbonyl groups, such as cyclohexylcarbonyl.

Examples of the aryl may include: monocyclic aromatic groups and aromatic condensed ring groups, such as phenyl, naphthyl and anthranyl.

Examples of the aralkyl may include: benzyl, pyridylmethyl and naphthomethyl.

Examples of the heterocyclic group may include: monocyclic heterocyclic groups, such as furyl, thienyl, pyrrolyl, imidazolyl and pyridyl; and condensed heterocyclic groups, such as indolyl, and amidinyl.

These substituents can be further substituted. In the case of the substitution, examples of the substituents may include: halogen, alkyl, amino, alkoxy, formyl, nitrile, nitro, aroyl, alkyloyl, optionally substituted aryl, optionally substituted aralkyl, and optionally substituted heterocyclic group, wherein the substituents for the optionally substituted aryl, aralkyl and heterocyclic group may include: halogen, allyl, amino, alkoxy, formyl, nitrile, aroyl, alkylonyl, optionally substituted aryl, optionally substituted aralkyl and optionally substituted heterocyclic groups, but these are not exhaustive. Specific examples thereof may include those enumerated above.

Further, examples of the condensed ring which can be formed by a combination of the above-mentioned adjacent one or more pairs of $R_1$–$R_{11}$ may include: single-ring structures and condensed ring structures, such as benzo, anthro, pyrido, pyrazino, imidazo, thieno, pyrazolo, and carbazolo.

Representative examples of the organic boron compound represented by the formula (1) are enumerated below by way of structural formulae, but they are not exhaustive. In the following structural formulae, some symbols are used for representing substituent groups, e.g., Me for methyl, Ph for phenyl and t-Bu for tert-butyl.

1

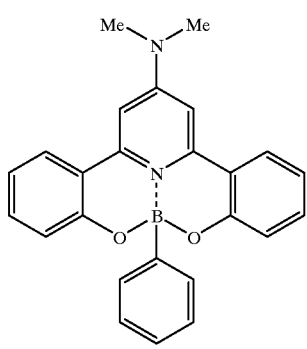

2

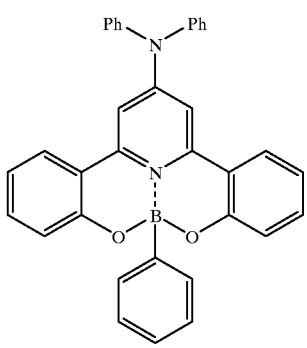

3

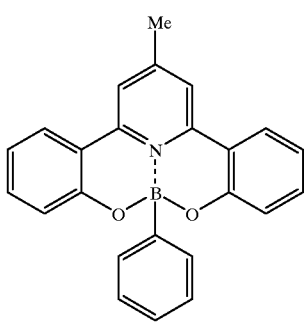

4

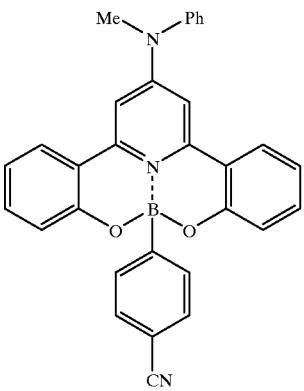

5

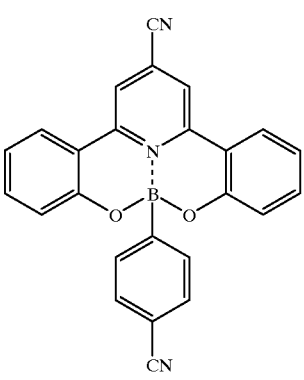

6

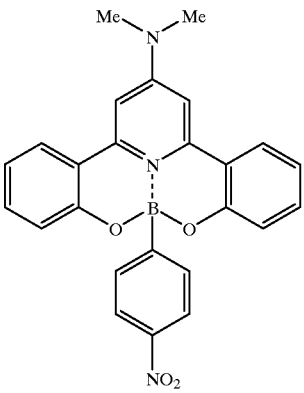

7

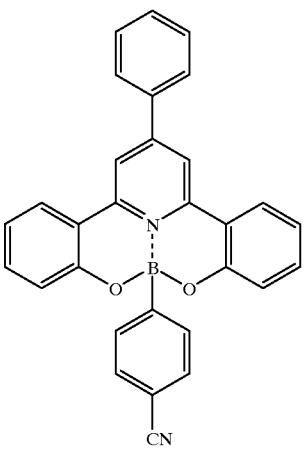

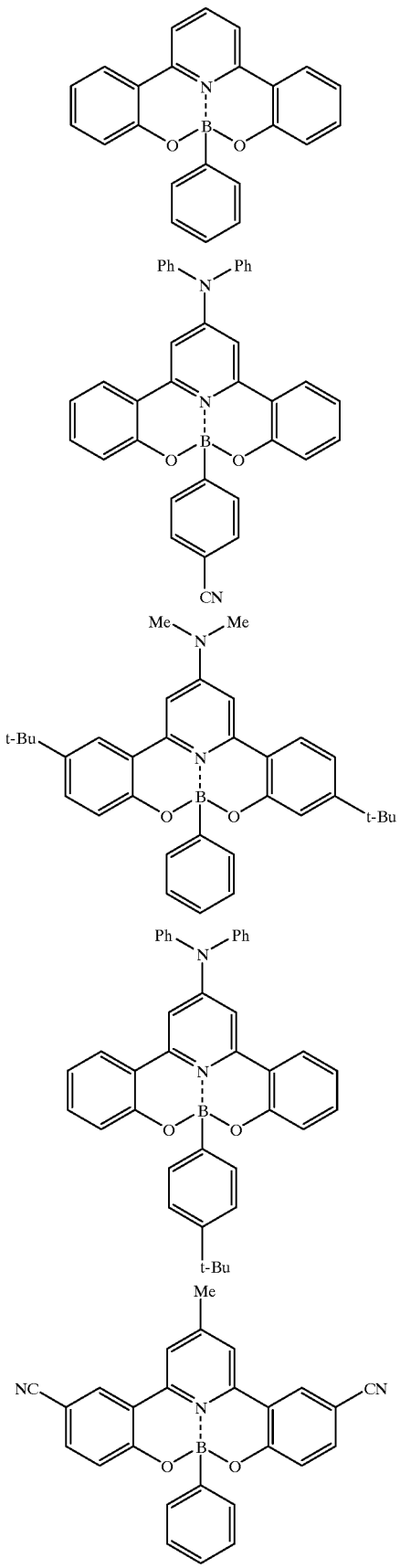

16
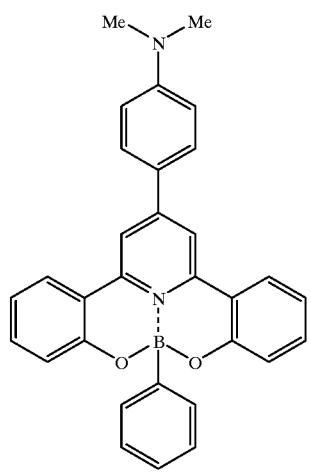
17
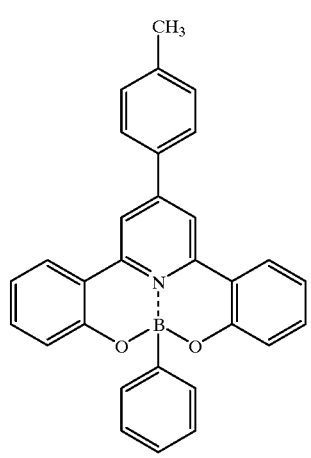
18
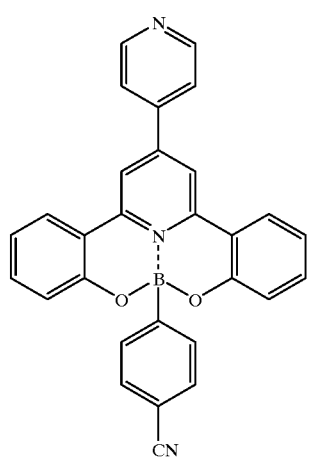
19
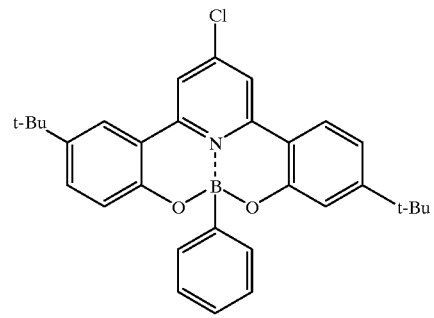
20
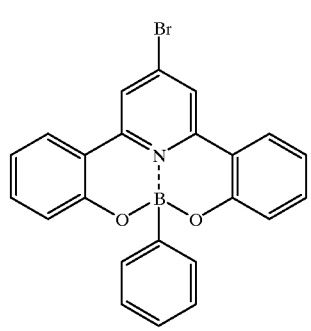
21
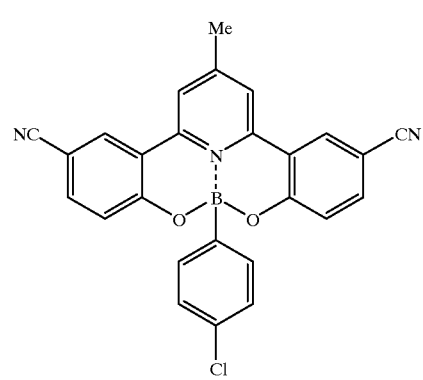
22
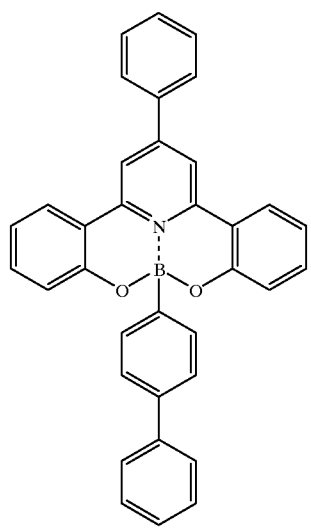

23
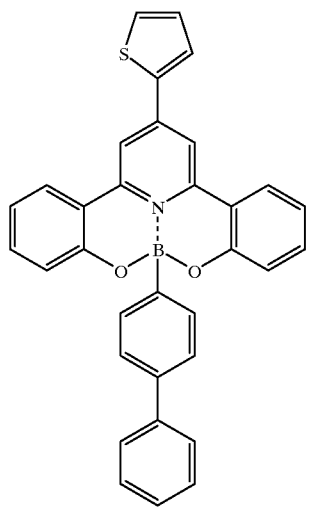
24
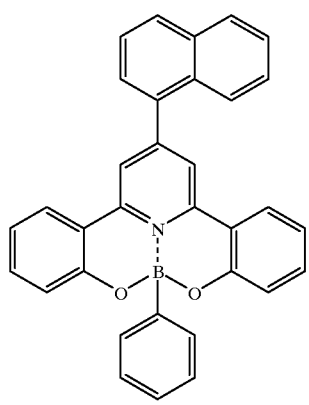
25
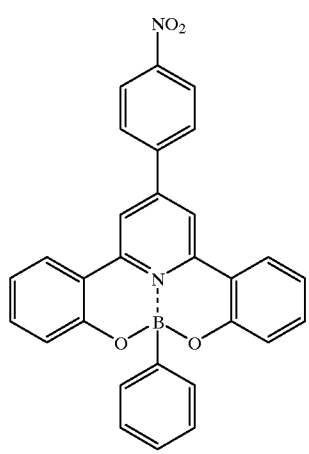
26
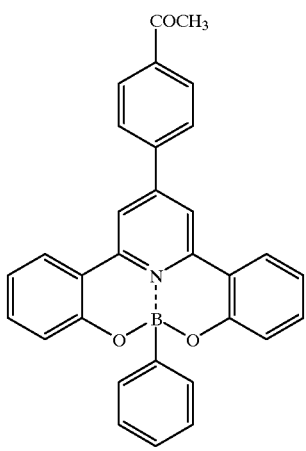
27
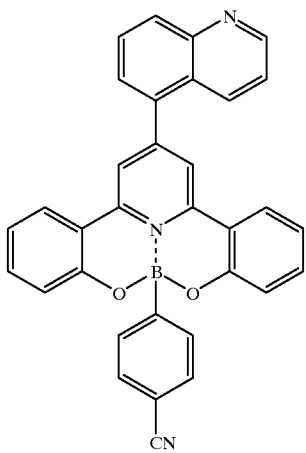
28
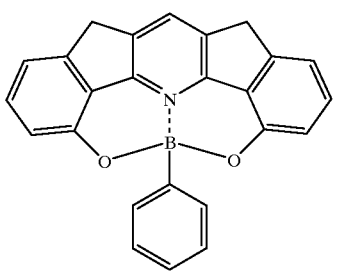
29
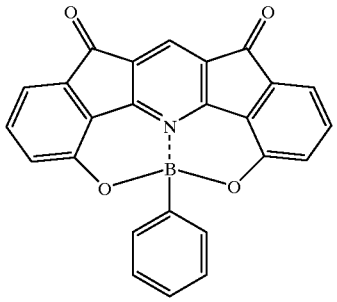

30
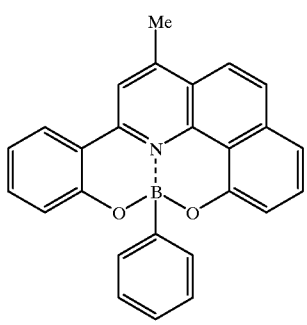
31
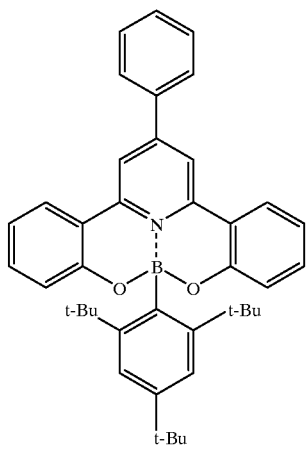
32
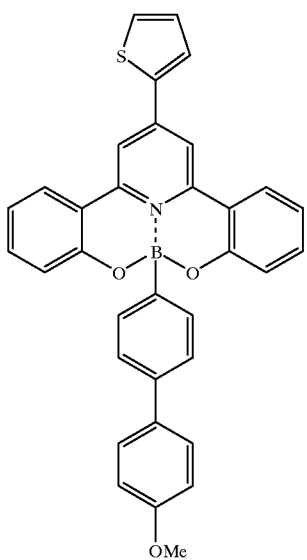
33
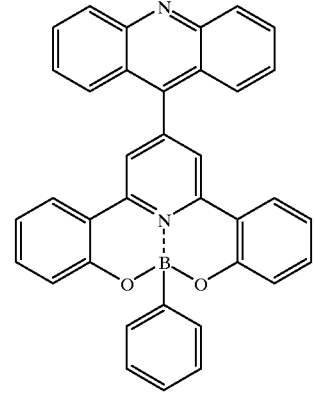
34
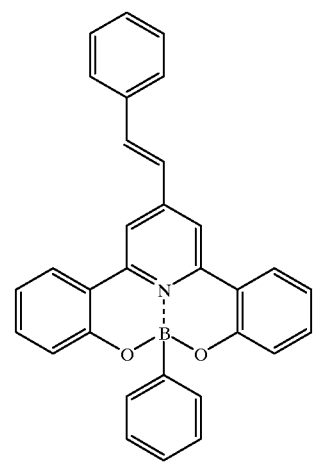
35
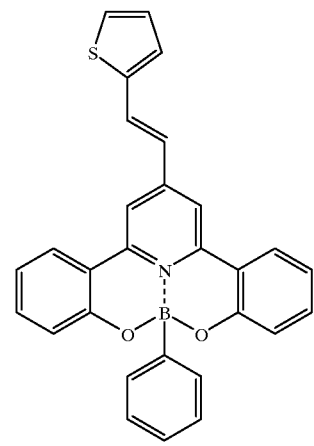

36

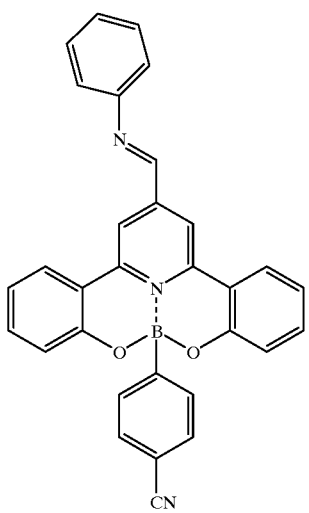

37

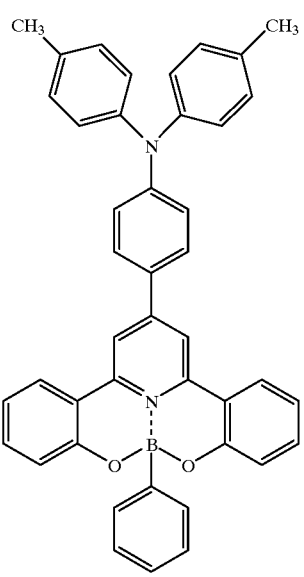

According to the process of the present invention, the above-mentioned organic boron compound of the formula (1) may be produced through a step of reacting an aromatic ketone compound, preferably a benzoyl ketone compound, with an aromatic ketone compound, preferably a benzoyl ketone compound, or an aromatic aldehyde compound, preferably a benzaldehyde compound, in the presence of ammonium acetate, and a step of reacting the reaction product of the above step with an organic boric acid compound, preferably an aromatic boric acid compound.

According to a more specific embodiment, the organic boron compound of the formula (1) may be synthesized by subjecting a ketone compound X and a ketone compound Y to a ring-addition reaction together with ammonium acetate to form a pyridine compound and reacting the pyridine compound with a boric acid compound to cause an addition reaction.

More specifically, a ketone compound X of formula (2) below:

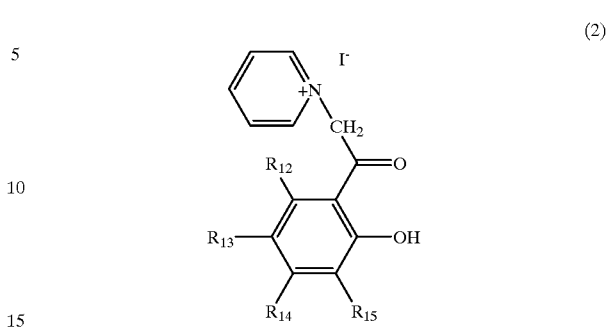

(wherein $R_{12}$–$R_{15}$ represent substituents identical to those represented by $R_1$–$R_{11}$ in the formula (1)), is reacted with a ketone compound Y of formula (3) below:

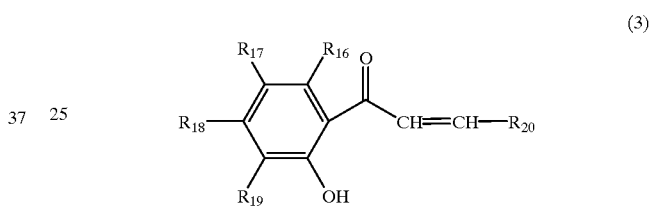

(wherein $R_{16}$–$R_{20}$ represent substituents identical to those represented by $R_1$–$R_{11}$ in the formula (1)) together with ammonium acetate to form a pyridine compound of a formula (4) below:

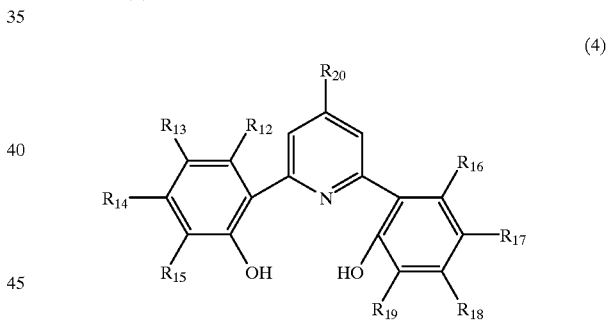

(wherein $R_{12}$–$R_{20}$ are identified above).

The pyridine compound of the formula (4) above can also be synthesized through the following steps.

A ketone compound X of formula (5) below:

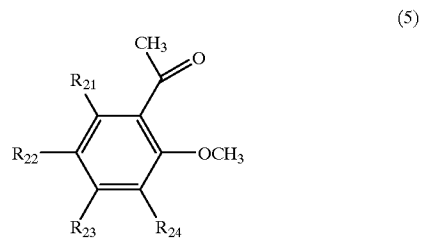

(wherein $R_{21}$–$R_{24}$ are substituents identical to those represented by $R_1$–$R_{11}$ in the formula (1)), is reacted with an aldehyde compound of formula (6) below:

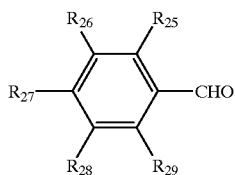
(6)

(wherein $R_{25}$–$R_{29}$ are substituents identical to those represented by $R_1$–$R_{11}$ in the formula (1)) together with ammonium acetate to form a compound represented by formula (7) below:

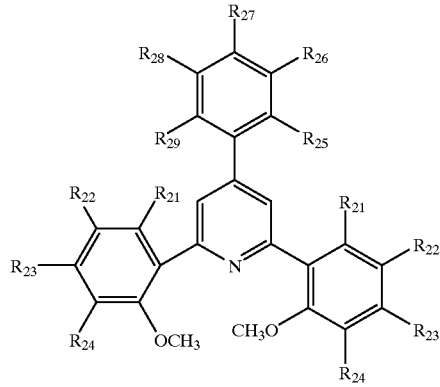
(7)

The compound of the formula (7) is hydrolyzed under an acidic condition to form a compound of formula (8) below (which can also be represented by the above formula (4)):

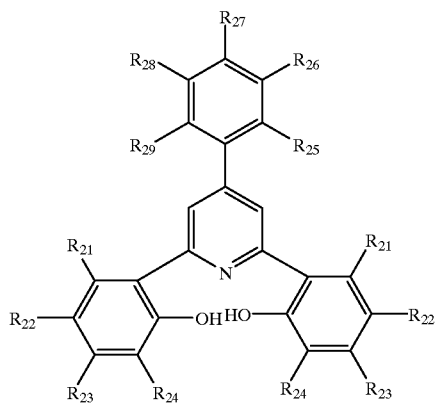
(8)

(wherein $R_{21}$–$R_{29}$ are identified above).

The compound of the formula (4) or formula (8) above is reacted with a boric acid compound of formula (9) below:

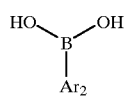
(9)

(wherein Ar2 is a substituent identical to the one represented by $Ar_1$ in the formula (1)) to form a compound of formula (10) or (11) below:

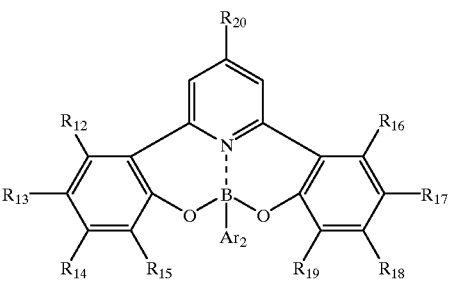
(10)

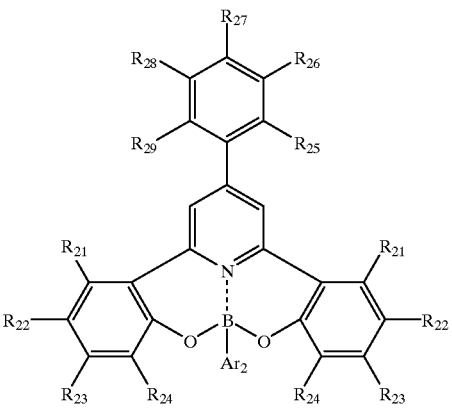
(11)

The compound of the formula (10) or (11) is substantially identical to the one represented by the formula (1).

In the above-described reaction scheme, the compound of formula (2) and the compound of formula (3) may preferably be reacted in a molar ratio of 2:5 to 5:2. Ammonium acetate may preferably be used in an amount of at least 10 times the compound of formula (2) in terms of the molar ratio. The reaction may preferably be effected in a solvent, such as acetic acid, at 70–100° C. for 3–20 hours.

Further, the compound of formula (5) and the compound of formula (6) may preferably be reacted in a molar ratio of 1:1 to 4:1. Ammonium acetate may preferably be used in an amount of at least 10 times the compound of formula (5) in terms of the molar ratio. The reaction may preferably be effected in a solvent, such as acetic acid, at 70–100° C. for 3–20 hours.

The hydrolysis of the compound of formula (7) may preferably be effected by using an acid, such as hydrobromic acid at 70–100° C. for 3–10 hours.

The compound of formula (4) or (8) and the compound of formula (9) may preferably be reacted in a molar ratio of 1:1 to 1:4. The reaction may preferably be effected in a solvent, such as acetic acid, at 20–100° C. for 1–10 hours.

The organic boron compound of the present invention exhibits a strong fluorescence emission. Accordingly, it is suitably used not only in an organic luminescence device as described below, but is also, e.g., as a reagent for quantitative analysis of boric acid, etc.

According to an aspect of the present invention, there is provided an organic luminescence device comprising a pair of electrodes and a layer comprising the organic boron compound of the formula (1) disposed between the electrodes.

In the organic luminescence device of the present invention, the organic compound layer comprising the above-mentioned organic boron compound of formula (1) may be formed between a pair of anode and cathode (electrodes) by vacuum deposition or by a wet-coating process. The organic compound layer may preferably be formed in a thickness of at most 10 μm, more preferably at most 0.5 μm, further preferably 0.01–0.5 μm.

It is also possible to provide a luminescence device of the present invention by disposing between a pair of electrodes a plurality of layers including at least one layer comprising the above-mentioned organic boron compound of the formula (1). According to the present invention, by appropriately selecting an organic boron compound from a range of compounds represented by the formula (1), it is possible to provide a luminescence device emitting a desired color of luminescence.

Figure 2:
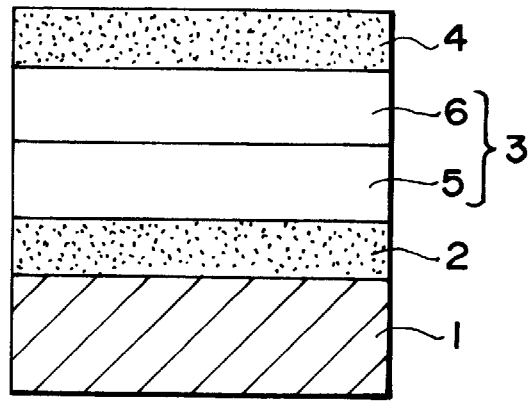
Figure 3:
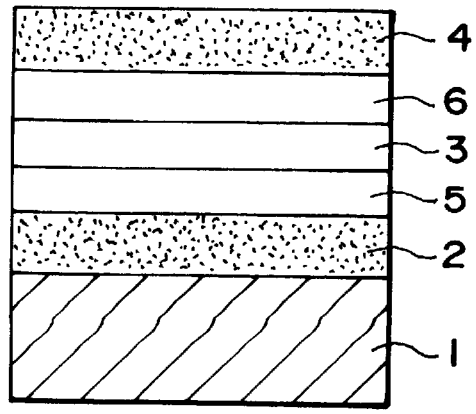

In other words, with reference to the drawings, the organic compound layer constituting the organic luminescence device of the present invention may have a single-layer structure as shown in FIG. 1 or a laminate structure of two or more layers as shown in FIGS. 2 and 3.

More specifically, FIG. 1 is a schematic sectional view illustrating an embodiment of the organic luminescence device of the present invention. Referring to FIG. 1, the organic luminescence device includes a substrate 1, and an anode 2, a luminescence layer 3 and a cathode disposed in this order on the substrate 1 so as to form a laminate structure. The luminescence layer 3 may comprise a single species of luminescent material exhibiting a hole-transporting function, an electron-transporting function and a luminescence function in combination or a mixture of plural compounds exhibiting these functions, respectively. The luminescence layer 3 may have a thickness of 5 nm to 1 μm, preferably 10–500 nm.

FIG. 2 is a sectional view showing a laminate structure of another embodiment of the organic luminescence device. Referring to FIG. 2, the organic luminescence device includes a substrate 1, and an anode 2, a hole-transporting layer 5, an electron-transporting layer 6 and a cathode 4 disposed successively in this order on the substrate 1 so as to form a laminate structure, either one or both of the hole-transporting layer 5 and the electron-transporting layer 6 may contain a luminescent material also having a hole-transporting function and/or an electron-transporting function, respectively, for constituting a luminescence layer 3 in combination. One of the layers 6 and 5 may contain a material having no luminescent function but having a good electron-transporting or hole-transporting function. Each of the hole-transporting layer 5 and the electron-transporting layer 6 may have a thickness of 5 nm to 1 μm, preferably 10–500 nm.

FIG. 3 is a sectional view showing still another embodiment of the organic luminescence device of the present invention. Referring to FIG. 3, the organic luminescence device includes a substrate 1, and an anode 2, a hole-transporting layer 5, a luminescence layer 3, an electron-transporting layer 6 and a cathode 4 disposed successively in this order on the substrate 1 to form a laminate structure. In this embodiment, the carrier transporting functions and the luminescent function of the organic compound layer are separated and assigned to the respective layers. Each of the hole-transporting layer 5, the luminescence layer 3 and the electron-transporting layer 6 may contain a single species or plural species of compounds showing respectively expected functions so as to exhibit desired performances. More specifically, in the case of using plural species of compounds in combination, a lot of latitude is provided in selection of materials for each layer, and various compounds having different emission wavelengths can be used to provide a variety of luminescence hues.

Further, as the carriers and excitons are effectively confined in the central luminescence layer 3, it is possible to increase the luminescence efficiency.

In the embodiment of FIG. 3, each of the hole-transporting layer 5, the luminescence layer 3 and the electron-transporting layer 6 may have a thickness of 5 nm–1 μm, preferably 10–500 nm.

It is to be understood however that FIGS. 1–3 described above merely show basic structures of the organic luminescence device according to the present invention, and various modifications thereof are possible. For example, between the organic compound layer(s) and the electrodes (anode and cathode), it is possible to dispose an electron injection layer (on the cathode side), a hole injection layer (on the anode side), an insulating layer, an adhesive layer, or an interference layer. Further, the hole-transporting layer 5 can be divided into two layers with different ionization potentials.

The layer comprising the organic boron compound of the formula (1) can be used to constitute any of the hole-injecting and transporting layer, the electron-transporting layer and the luminescence layer. However, the organic boron compound of the formula (1) can also be used to constitute such a functional layer, as desired in combination with a known hole-transporting compound, electron-transporting compound or luminescent compound, examples of which are enumerated hereinbelow.

Hole-transporting compounds

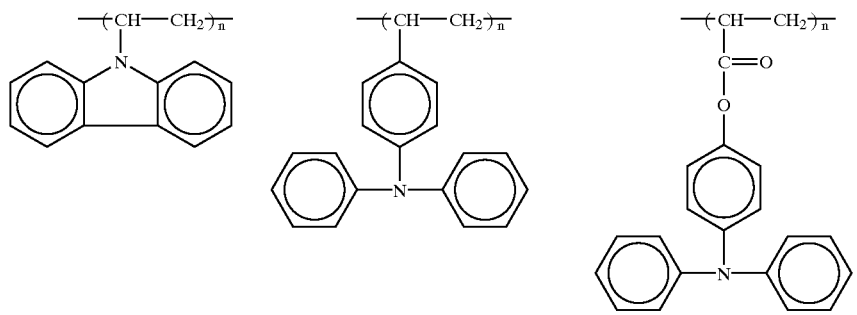

-continued
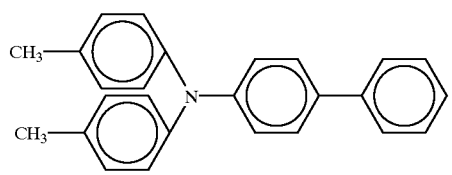
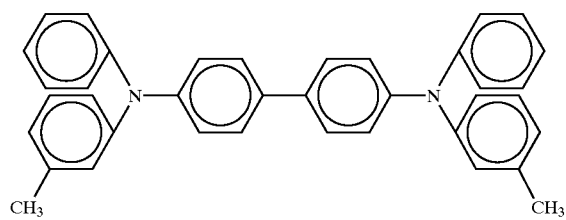
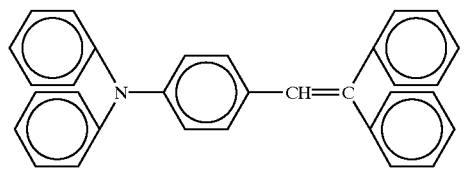
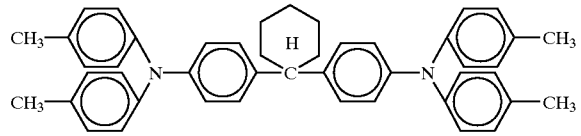
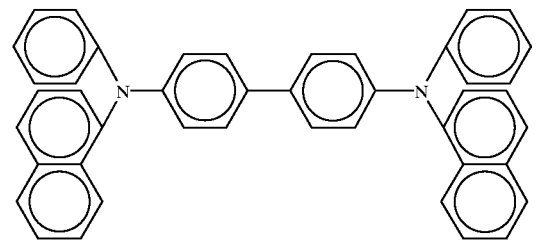
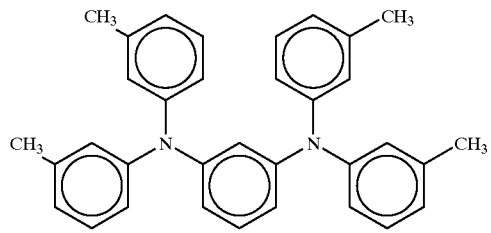
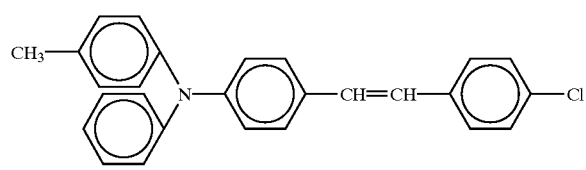
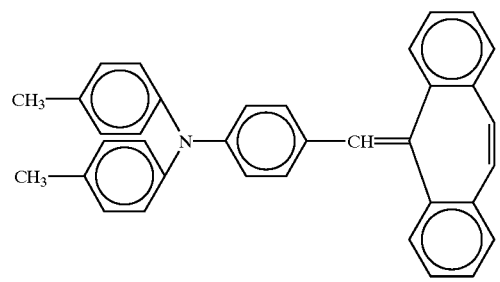
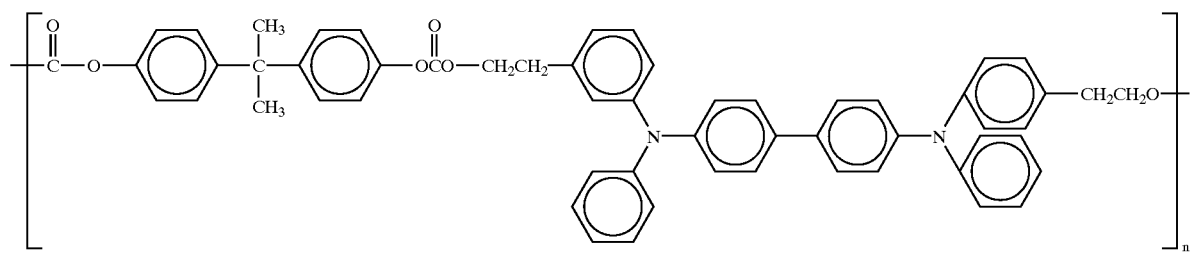
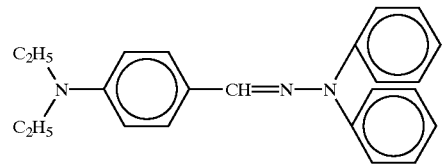
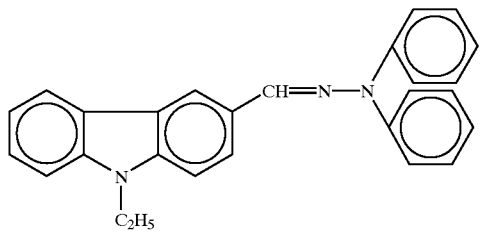
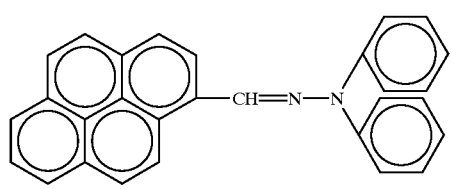
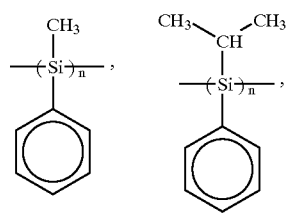
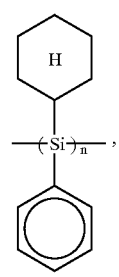
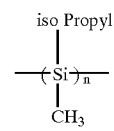

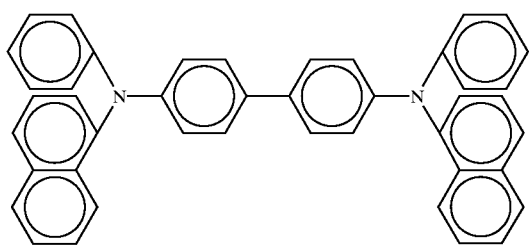
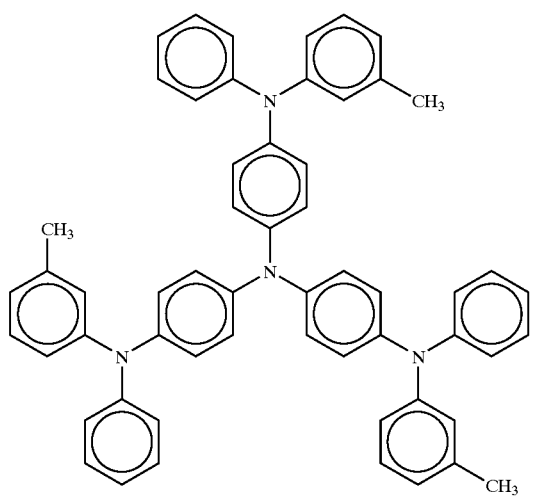
Electron-transporting compounds
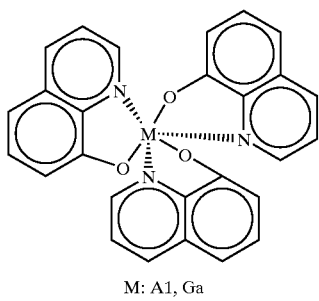
M: Al, Ga
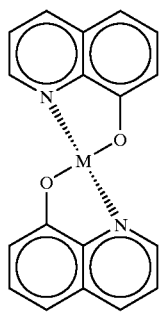
M : Zn, Mg, Be
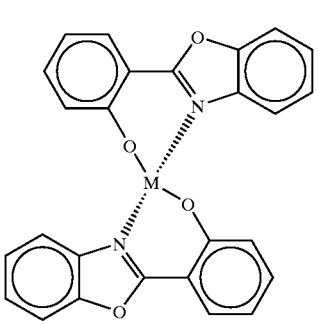
M : Zn, Mg, Be
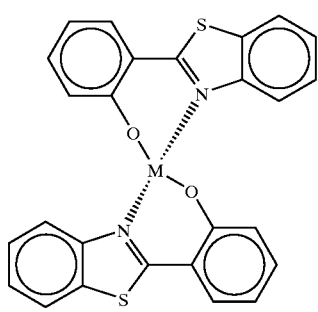
M : Zn, Mg, Be
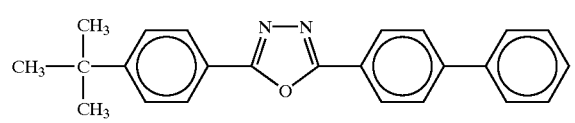
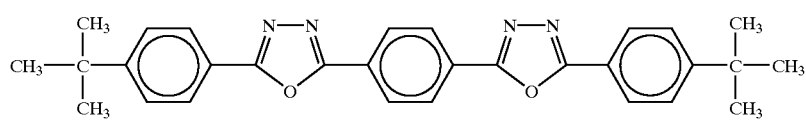
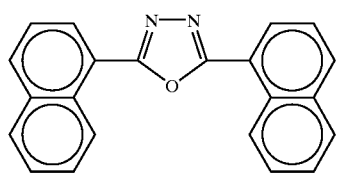
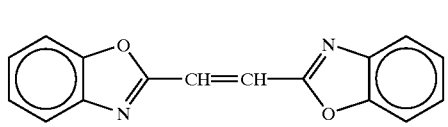
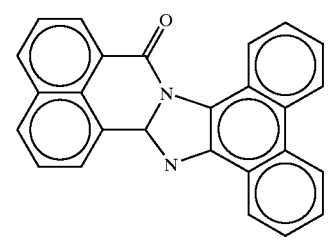

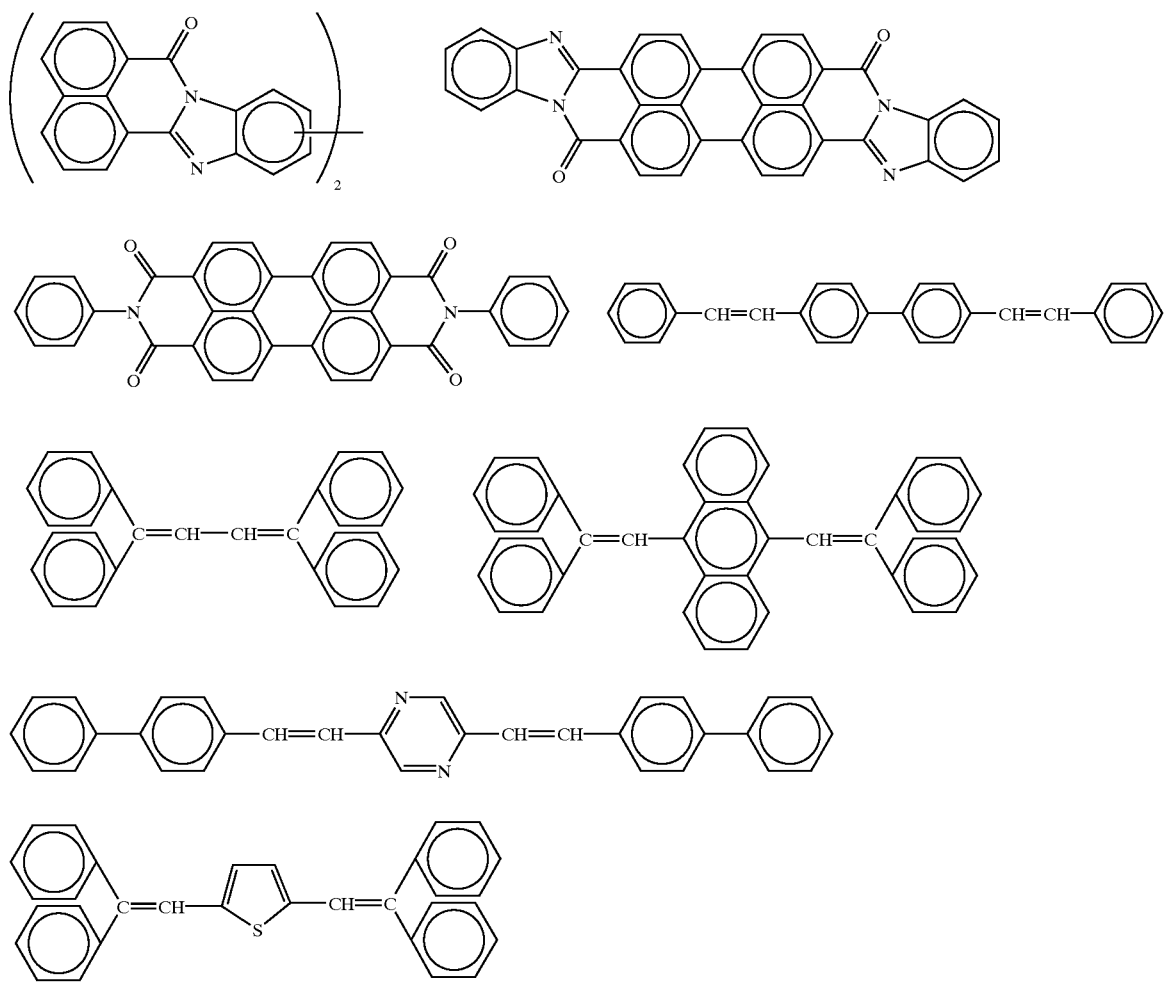
Luminescent material (dopant)
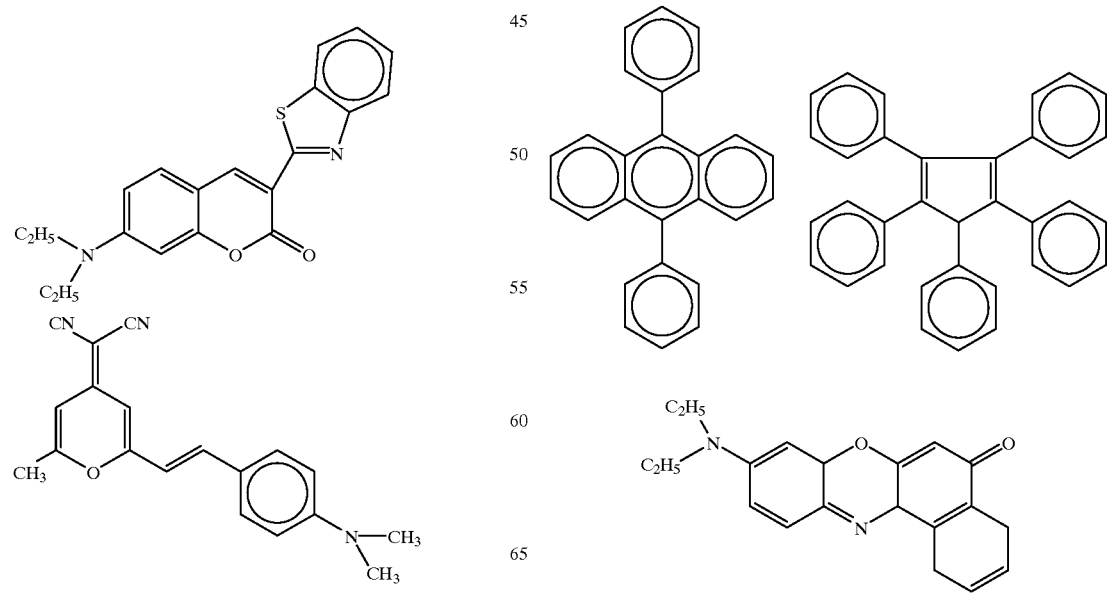

-continued

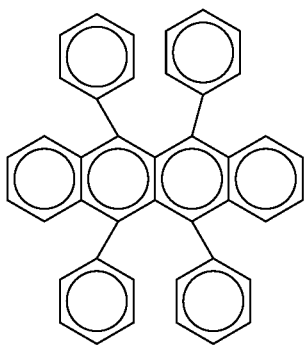

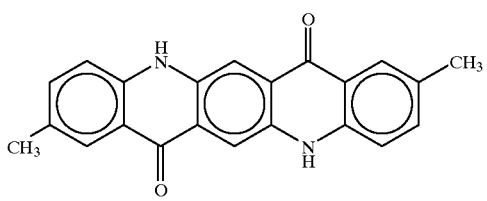

As mentioned above, the organic compound layer containing the organic boron compound of the formula (1) or other organic compound layers may be formed into film by vacuum deposition or coating of a solution of the relevant compound in an appropriate solvent. In the case of the solution coating, the organic compound can be used in mixture with an appropriate binder resin to form a film. In this case, the organic compound, inclusive of the organic boron compound of the formula (1) may for example be used in 0.01–20 wt. parts, preferably, 0.1–10 wt. parts, per 1 wt. part of the binder resin.

The binder resin used for the above purpose may be selected from a wide variety of scope. Examples thereof may include: polyvinyl carbazole resin, polycarbonate resin, polyester resin, polyarylate resin, polystyrene resin, acrylic resin, methacrylic resin, butyral resin, polyvinyl acetal resin, diallyl phthalate resin, phenolic resin, epoxy resin, silicone resin, polysulfone resin, and urea resin. These resins may be used singly or in combination of two or more species or in the form of copolymers.

As a material for the anode (2 shown in FIGS. 1–3), it is preferred to use one having as large a work function as possible, examples of which may include: metals, such as gold, platinum, nickel, palladium, cobalt, selenium and vanadium, and their alloys; metal oxides, such as tin oxide, zinc oxide, indium tin oxide (ITO), and indium zinc oxide; and electroconductive polymers, such as polyaniline, polypyrrole, polythiophene, and polyphenylene sulfide. These compounds may be used singly or in combination of two or more species.

On the other hand, as a material for the cathode 4 shown in FIGS. 1–3, it is preferred to use one having a small work function, examples of which may include: metals, such as lithium, sodium, potassium, calcium, magnesium, aluminum, indium, silver, lead, tin and chromium, and their alloys. It is also possible to use a metal oxide, such as indium tin oxide (ITO). The cathode may be formed in a single layer or a lamination of plural layers.

The substrate 1 shown in FIGS. 1—3 for the organic luminescence device of the present invention may include an opaque substrate of metal, ceramics, etc., and a transparent substrate of glass, quartz, plastics, etc. It is possible to form the substrate with a color filter film, a fluorescent color conversion film, a dielectric reflection film, etc., thus controlling emitted luminescent light.

In order to prevent contact with oxygen and/or moisture, the organic luminescence device of the present invention may further include a protective layer or a sealing layer. Examples of the protective layer may include: an inorganic film of diamond, metal oxide, metal nitride, etc.; a polymer film of fluorine-containing resin, polyparaxylene, polyethylene, silicone resin, polystyrene, etc., and a film of light-curable resin. It is also possible to effect packaging of the organic luminescence device per se with a sealing resin while covering the organic luminescence device with glass, gas-impermeable film, metal, etc.

Hereinbelow, the present invention will be described more specifically based on Examples.

EXAMPLE 1

The above-listed example compound No. 37 was synthesized in the following manner (the reaction scheme is summarized at the end).

3.01 g (10 mmol) of 4-[bis(4'-methylphenyl)-amino] benzaldehyde, 3.00 g (20 mmol) of o-methoxyacetophenone and 14 g of ammonium acetate were added to 50 ml of acetic acid, and the mixture was subjected to 12 hours of refluxing under heating. After being cooled to room temperature, the reaction product was poured ito 200 ml of water and was extracted two times with 100 ml each of chloroform. The resultant chloroform layer was condensed under a reduced pressure, and the condensate was re-crystallized from a solvent mixture of benzene/hexane (=1/1) to obtain 1.30 g of 2,6-bis(2'-methoxyphenyl)-4-[4"-bis(4'"-methylphenyl) amino]phenylpyridine. Further, the filtrate after the re-crystallization was subjected to silica gel column chromatography with benzene as the eluent to recover 0.79 g of the same compound. Yield: 37.2%.

Then, 1.12 g (2 mmol) of the 2,6-bis(2'-methoxyphenyl)-4-[4"-(4'"-methylphenyl)amino]-phenylpyridine was added to 30 ml of 47%-hydrobromic acid, followed by 6 hours of refluxing under heating. After being cooled to room temperature, the reaction liquid was poured into 100 ml of water and extracted with 200 ml of chloroform. The resultant chloroform layer was washed first with 10%-sodium carbonate aqueous solution and then with water. Then, the chloroform was distilled off under a reduced pressure, and the residue was subjected to silica gel column chromatography with chloroform as the eluent to obtain 0.46 g (yield: 42%) of 2,6-bis(o-hydroxyphenyl)-4-[4"-bis(4'"-methylphenyl)amino]phenylpyridine.

Then, 0.53 g (1 mmol) of the 2,6-bis(o-hydroxyphenyl)-4-[4"-bis(4'"-methylphenyl)amino]-phenylpyridine was dissolved in 30 ml of acetic acid under heating at 50-60° C., and 0.15 g (1.25 mmol) of phenylboric acid was added thereto under stirring at room temperature, to result in a yellowish precipitate ca. 10 mm later. The stirring was performed for 4 hours, and the precipitate was washed with water to obtain 0.47 g (yield: 75%) of substantially pure phenylboric acid ester of 2,6-bis(o-hydroxyphenyl)-4-[4"-bis(4'"-methylphenyl)amino]phenylpyridine (Compound No. 37).

The above reaction scheme is summarized as follows.

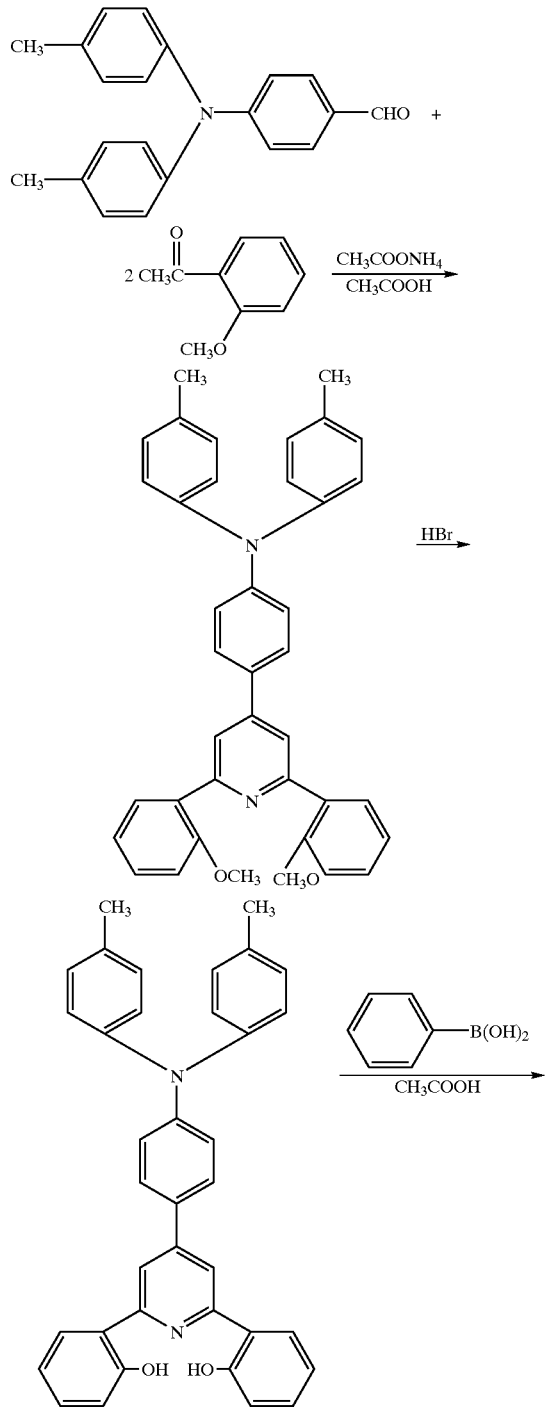

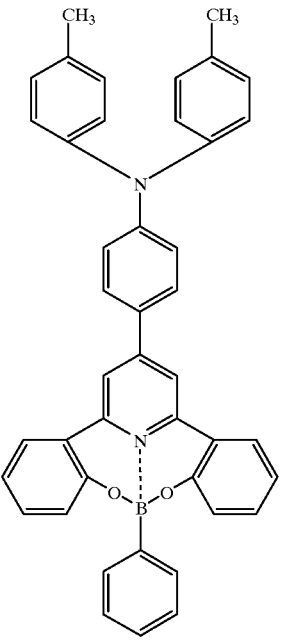

EXAMPLE 2

The above-listed example compound No. 16 was synthesized in the following manner.

1.63 g (5 mmol) of 2-hydroxyphenacyl-pyridinium iodide, 0.53 g (2 mmol) of 1-(2-hydroxyphenyl)-3-(4-dimethylaminophenyl)-2-propen-1-one and 4 g of ammonium acetate were added to 4 ml of acetic acid, and the mixture was subjected to refluxing under heating for 5 hours. After being cooled to room temperature, the reaction mixture was poured to 50 ml of water and extracted two times with 30 ml each of chloroform. The chloroform was distilled off under a reduced pressure, and the residue was subjected to silica gel column chromatography with chloroform as the eluent to obtain 0.61 g (yield: 79%) of 2,6-bis(2-hydroxyphenyl)-4-(4-dimethylaminophenyl)pyridine. (Incidentally in case where the reaction residue was subjected to re-crystallization from 30 ml of ethanol, the 2,6-bisphenolpyridine product was recovered at a yield of 64%.)

Then, 0.38 g (1 mmol) of the 2,6-bis(2-hydroxyphenyl)-4-(4-dimethylaminophenyl)pyridine was dissolved in 30 ml of acetic acid, and 0.15 g (1.25 mmol) of phenylboric acid was added thereto, followed by stirring at room temperature to result in a precipitate within ca. 10 min . The stirring was continued for 4 hours, and the precipitate was recovered by filtration and washed with water until the washing liquid became neutral, thereby obtaining 0.37 g (yield: 80%) of substantially pure phenylboric acid ester of 2,6-bis(2-hydroxyphenyl)-4-(4-dimethylaminophenyl)pyridine (Compound No. 16).

The above reaction scheme is summarized as follows:

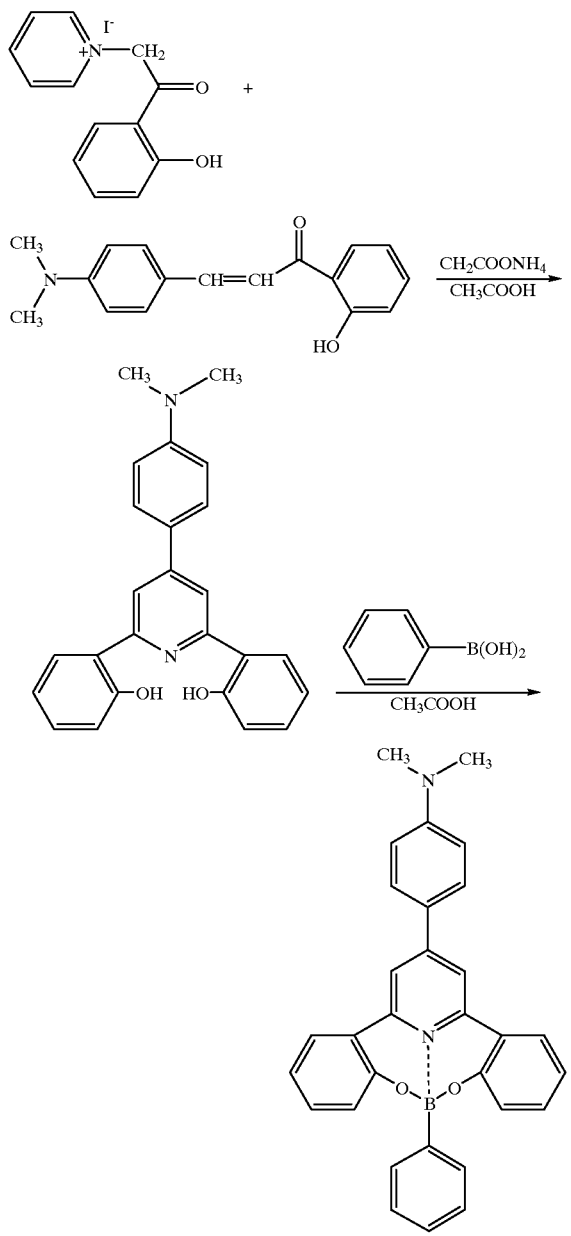

EXAMPLE 3

The above-listed example compound No. 17 was synthesized in the following manner.

0.35 g (1 mmol) of 2,6-bis(o-hydroxyphenyl)-4-(p-methylphenyl)pyridine was dissolved in 30 ml of acetic acid, and 0.15 g (1.25 mmol) of phenylboric acid was added thereto, followed by stirring at room temperature to result in a precipitate within ca. 10 min. The stirring was continued for 8 hours, and the precipitate was recovered by filtration and washed with water until the washing liquid became neutral, thereby obtaining 0.32 g (yield: 74%) of substantially pure phenylboric acid ester of 2,6-bis(o-hydroxyphenyl)-4-(p-methylphenyl)pyridine.

The reaction scheme is represented as follows.

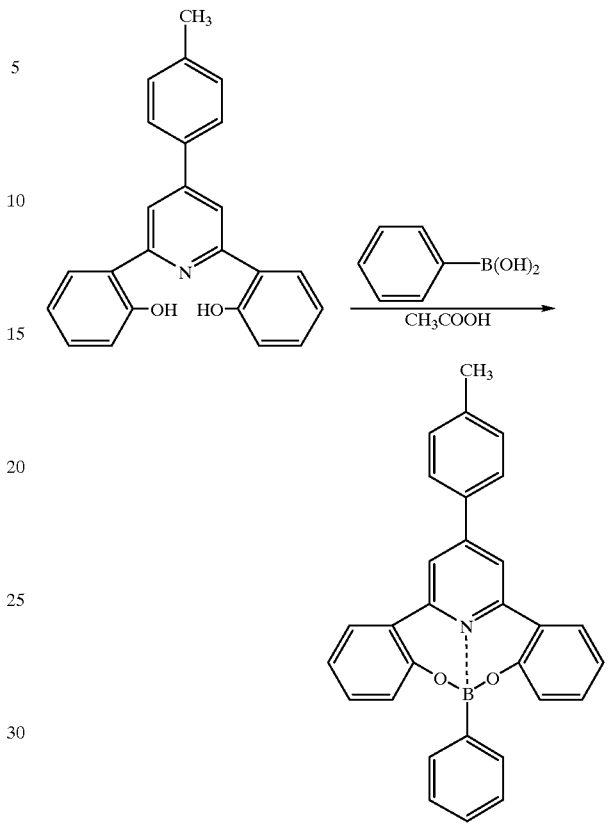

EXAMPLE 4

An organic boron compound of a structure as shown in FIG. 2 was prepared in the following manner.

A 1.1 mm-thick glass substrate coated with a 120 nm-thick film of ITO (indium tin oxide) formed by sputtering was successively washed with acetone and isopropyl alcohol (IPA) under application of ultrasonic wave and then washed with IPA under boiling, followed by cleaning by UV/ozone (i.e., irradiation with ultraviolet rays in the ozone-containing atmosphere), to obtain a transparent conductive substrate (including a substrate 1 and an ITO anode 2 formed thereon).

The transparent conductive substrate was coated by vacuum deposition first with N,N-diphenyl-N,N'-m-tolyl-4,4'-diamino-1,1'-biphenyl (hereinafter called "TPD") (hole-transporting material) in a thickness of 500 Å (layer 5), then the above-listed Compound No. 2 in a thickness of 500 Å (layer 6) and then Al in a thickness of 1500 Å (cathode 4) to prepare a luminescence device. The device caused luminescence of green at luminances of 150 cd/m$^2$ at 9 volts.

EXAMPLE 5

An ITO-coated transparent conductive substrate identical to the one used in Example 4 was first coated by vacuum deposition first with TPD in a thickness of 500 Å (layer 5), then with Compound No. 16 in a thickness of 500 Å (layer 6) and then with Al in a thickness of 1500 Å (cathode 4) to prepare an organic luminescence device. The device caused luminescence of green at luminances of 200 cd/m$^2$ at 5 volts and 1500 cd/m$^2$ at 9 volts.

EXAMPLE 6

An ITO-coated transparent conductive substrate identical to the one used in Example 4 was coated first by vacuum deposition with TPD in a thickness of 500 Å, then by co-vavcuum deposition with Compound No. 16 and 1% thereof of coumarin 6 (as dopant) in a thickness of 300 Å, further by vacuum deposition with Compound No. 16 in a thickness of 200 Å and then by vacuum deposition with Al in a thickness of 1500 Å (cathode) to prepare an organic luminescence device. The device caused luminescence of green at luminances of 240 cd/m$^2$ at 5 volts and 300 cd/m$^2$ at 9 volts. As is understood from comparison with Example 5, the luminance at 9 volts was remarkably increased by adding coumarin 6 as a dopant.

EXAMPLE 7

An ITO-coated transparent conductive substrate was coated by vacuum deposition first with TPD in a thickness of 500 Å, then with Compound No. 17 in a thickness of 500 Å and then with Al in a thickness of 1500 Å (cathode) to prepare an organic luminescence device. The device caused luminescence of yellow at luminances of 40 cd/m$^2$ at 5 volts and 500 cd/m$^2$ at 9 volts.

EXAMPLE 8

An ITO-coated transparent conductive substrate was coated by vacuum deposition first with TPD in a thickness of 500 Å, then with Compound No. 17 in a thickness of 500 Å, then with Al-Li alloy (Li content: 1 atom %) in a thickness of 100 Å (as an electron-injecting layer) and then with Al in a thickness of 1500 Å (cathode) to prepare an organic luminescence device. The device caused luminescence of green at luminances of 40 cd/m$^2$ at 5 volts and 500 cd/m at 9 volts.

As is understood from comparison with Example 7, the provision of the electron-transporting layer of Al-Li alloy did not resulted in a substantial difference in luminance. This means that Compound No. 17 (as an example of organic boron compound of the present invention) also exhibited an excellent electron-injecting function.

EXAMPLE 9

An ITO-coated transparent conductive substrate was coated by vacuum deposition first with TPD in a thickness of 500 Å (layer 5), then with tris(8-quinolinolato)aluminum complex in a thickness of 500 Å (luminescence layer 3 in FIG. 3), then with Compound No. 17 in a thickness of 20 Å (electron-injecting layer 6) and then with Al in a thickness of 1500 Å (cathode 4) to prepare an organic luminescence device.

Comparative Example

An ITO-coated transparent conductive substrate was coated by vacuum deposition first with TPD in a thickness of 500 Å (layer 5), tris(8-quinolinolato) aluminum complex in a thickness of 500 Å (luminescence layer 3 or electron-injecting layer 6) and then with Al in a thickness of 1500 Å (cathode 4) to provide an organic luminescence device.

Figure 4:
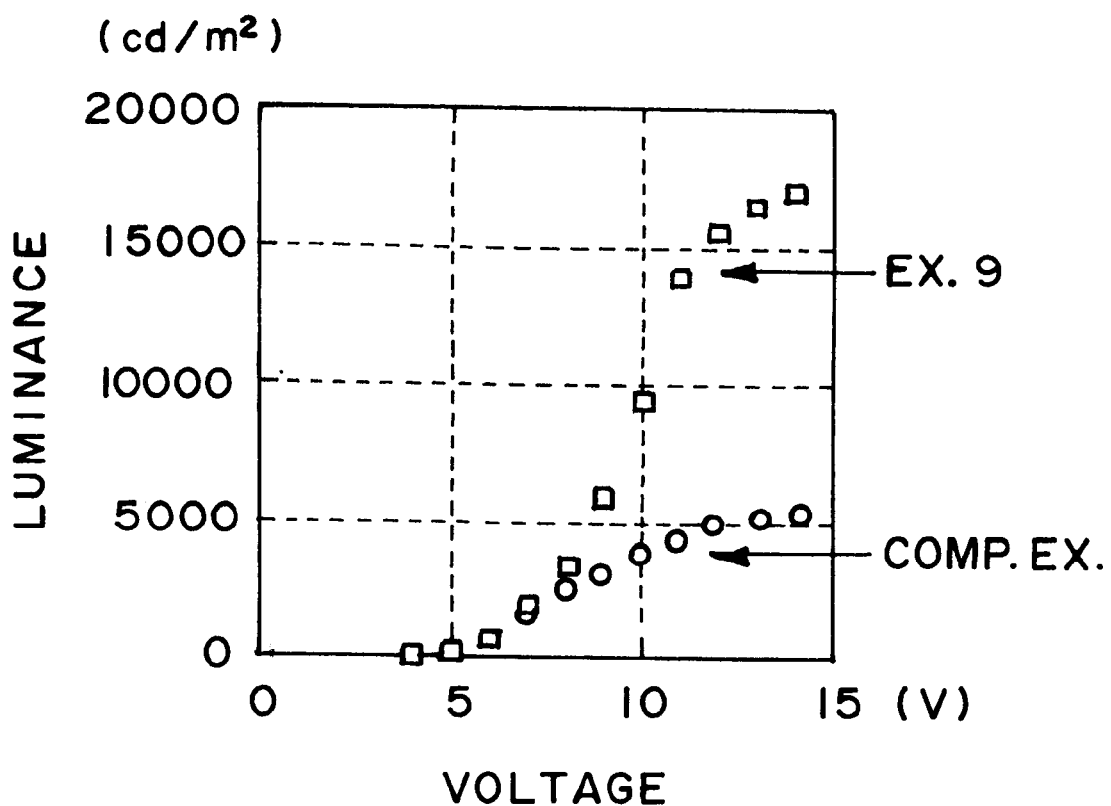
FIG. 4 is a graph showing voltage-luminescence characteristics of organic luminescence device of Example 9 and Comparative Example.

The devices of Example 9 and Comparative Example prepared above both caused luminescence of green and exhibited voltage-luminance characteristics shown in FIG. 4, which show that Compound No. 17 (as an example of the organic boron compound of the present invention) provided a very effective electron-injecting layer.

As described above, according to the present invention, there is provided an organic boron compound of the formula (1) which is useful as a luminescence device material, particularly excellent in charge-transporting characteristics and useful for constituting a luminescence layer and/or an electron-transporting layer exhibiting excellent performances.

Moreover, the above organic boron compound can be produced easily and relatively inexpensively by the process for production thereof according to the present invention.

Further, the organic luminescence device of the present invention including a layer of the organic boron compound can exhibit luminescence of very high luminance at a low application voltage and thus exhibits excellent durability.

An organic layer comprising the organic boron compound of the present invention is useful as an electron-transporting layer and a luminescence layer and is also useful as an electron-injecting layer. The layer can be easily formed by vacuum deposition or casting and therefore allows easy and inexpensive production of a large area device.

What is claimed is:

1. An organic boron compound represented by formula (1) below:

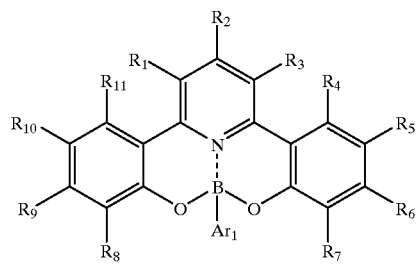

wherein Ar$_1$ denotes an optionally substituted aryl group or heterocyclic group; R$_1$–R$_{11}$ independently denote hydrogen, halogen, alkyl, alkenyl, amino, alkoxy, formyl, nitrile, aroyl, alkyloyl, aryl, aralkyl or heterocyclic group, each optionally substituted with the proviso that an adjacent one or more pairs of R$_1$–R$_{11}$ can form a condensed ring.

2. A process for producing an organic boron compound of the formula (1) according to claim 1, comprising:

(A) a step of reacting a ketone compound X with a ketone compound Y or an aldehyde compound in the presence of ammonium chloride, and (B) a step of reacting a product of the step (A) with an organic boric acid compound.

3. A process according to claim 2, wherein said ketone compound X is a benzoyl ketone compound.

4. A process according to claim 2, wherein said ketone compound Y is a benzoyl ketone compound.

5. A process according to claim 2, wherein said aldehyde compound is a benzaldehyde compound.

6. A process according to claim 2, wherein said ketone compound X is a compound represented by formula (2) below:

(2)

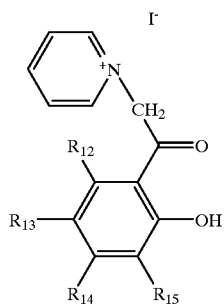

wherein $R_{12}$–$R_{15}$ represent substituents identical to those represented by $R_1$–$R_{11}$ in the formula (1), and said ketone compound Y is a compound represented by formula (3) below:

(3)

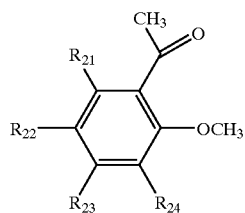

wherein $R_{16}$–$R_{20}$ represent substituents identical to those represented by $R_1$–$R_{11}$ in the formula (1).

7. A process according to claim 2, wherein said ketone compound X is a compound represented by formula (5) below:

(5)

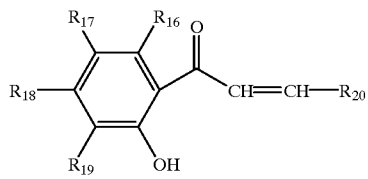

wherein $R_{21}$–$R_{24}$ are substituents identical to those represented by $R_1$–$R_{11}$ in the formula (1), and said aldehyde compound is a compound represented by formula (6) below:

(6)

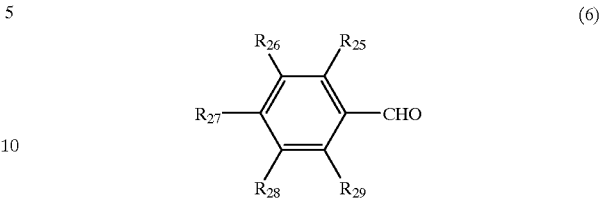

wherein $R_{25}$–$R_{29}$ are substituents identical to those represented by $R_1$–$R_{11}$ in the formula (1).

8. A process according to claim 2, wherein said organic boric acid compound is a compound represented by formula (9) below:

(9)

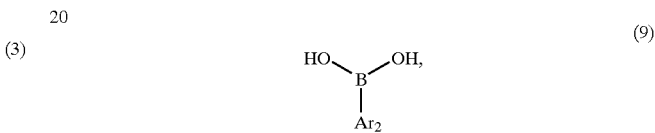

wherein $Ar_2$ is a substituent identical to the one represented by $Ar_1$ in the formula (1).

9. A process according to any of claims 2 to 8, wherein in the step (B), the product of the step (A) and the organic boric acid are reacted in a mol ratio of 2:5 to 5:2.

10. An organic luminescence device, comprising: a pair of electrodes comprising an anode and a cathode, and a layer of organic compound disposed between the electrodes; wherein the organic compound layer comprises an organic boron compound of the formula (1) according to claim 1.

11. An organic luminescence device according to claim 10, wherein said organic compound layer functions as a luminescence layer.

12. An organic luminescence device according to claim 10, wherein said organic compound layer functions as an electron-injecting layer.

13. An organic luminescence device according to claim 10, further including a hole-transporting layer.

* * * * *

UNITED STATES PATENT AND TRADEMARK OFFICE
CERTIFICATE OF CORRECTION

PATENT NO. : 6,461,749 B2
APPLICATION NO. : 09/818661
DATED : October 8, 2002
INVENTOR(S) : Kazunori Ueno et al.

It is certified that error appears in the above-identified patent and that said Letters Patent is hereby corrected as shown below:

COLUMN 1

Line 38, "(JP-A)" should read --JP-A--.

COLUMN 4

Line 5, "includes" should read --include--; and
Line 8, "group" should read --groups--.

COLUMN 25

Lines 18-26,

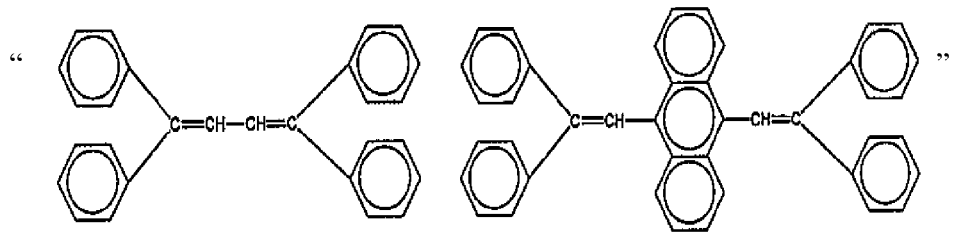

should read

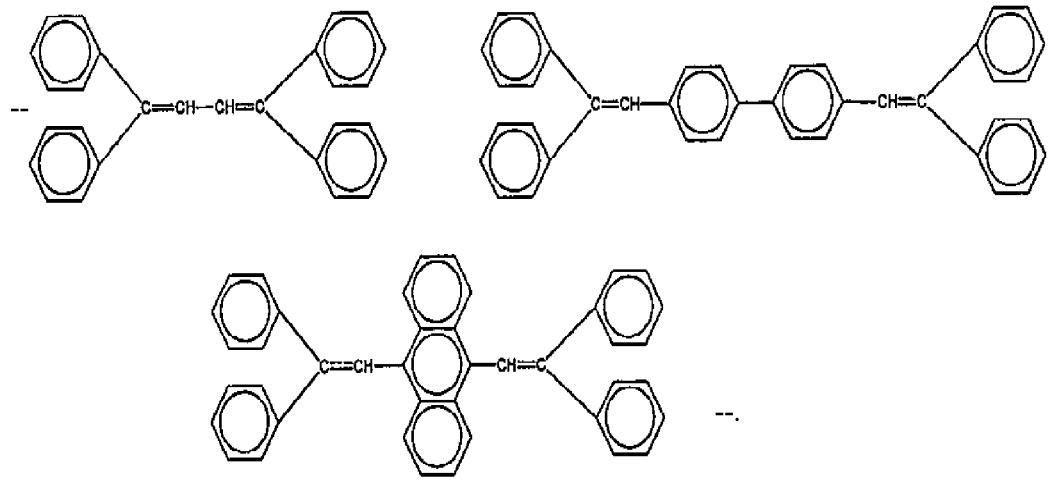

UNITED STATES PATENT AND TRADEMARK OFFICE
CERTIFICATE OF CORRECTION

PATENT NO. : 6,461,749 B2
APPLICATION NO. : 09/818661
DATED : October 8, 2002
INVENTOR(S) : Kazunori Ueno et al.

It is certified that error appears in the above-identified patent and that said Letters Patent is hereby corrected as shown below:

COLUMN 28

Line 39, "ito" should read --into--.

COLUMN 33

Line 5, "co-vavcuum" should read --co-vacuum--; and
Line 38, resulted" should read --result--.

Signed and Sealed this

Seventeenth Day of April, 2007

JON W. DUDAS
*Director of the United States Patent and Trademark Office*